(12) United States Patent
Hallbäck

(10) Patent No.: US 10,894,136 B2
(45) Date of Patent: Jan. 19, 2021

(54) CAPNOTRACKING OF CARDIAC OUTPUT OR EFFECTIVE PULMONARY BLOOD FLOW DURING MECHANICAL VENTILATION

(71) Applicant: MAQUET CRITICAL CARE AB, Solna (SE)

(72) Inventor: Magnus Hallbäck, Danderyd (SE)

(73) Assignee: MAQUET CRITICAL CARE AB, Solna (SE)

(*) Notice: Subject to any disclaimer, the term of this patent is extended or adjusted under 35 U.S.C. 154(b) by 288 days.

(21) Appl. No.: 16/098,398

(22) PCT Filed: May 3, 2016

(86) PCT No.: PCT/SE2016/050405
§ 371 (c)(1),
(2) Date: Nov. 1, 2018

(87) PCT Pub. No.: WO2017/192077
PCT Pub. Date: Nov. 9, 2017

(65) Prior Publication Data
US 2019/0201644 A1    Jul. 4, 2019

(51) Int. Cl.
*A61M 16/00*    (2006.01)
*A61B 5/029*    (2006.01)
(Continued)

(52) U.S. Cl.
CPC .......... *A61M 16/024* (2017.08); *A61B 5/029* (2013.01); *A61B 5/082* (2013.01); *A61B 5/087* (2013.01);
(Continued)

(58) Field of Classification Search
CPC ....... A61B 5/029; A61B 5/0813; A61B 5/082; A61B 5/0833; A61B 5/0836; A61B 5/087;
(Continued)

(56) References Cited

U.S. PATENT DOCUMENTS 4,949,724 A * 8/1990 Mahutte ................ A61B 5/029
                                                          600/526
5,971,934 A * 10/1999 Scherer ................ A61B 5/0836
                                                          128/923

(Continued)

FOREIGN PATENT DOCUMENTS

EP    1238631    9/2002
EP    2641536    9/2013

*Primary Examiner* — Joseph D. Boecker
(74) *Attorney, Agent, or Firm* — Fay Kaplun & Marcin, LLP

(57) ABSTRACT

A capnotracking method for continuous determination of cardiac output or EPBF of a mechanically ventilated subject includes the steps of measuring expiratory $CO_2$ of the subject and determining a first value of cardiac output or EPBF of the subject at a first point in time; controlling the mechanical ventilation of the subject to keep a level of venous $CO_2$ of the subject substantially constant between the first point in time and a second point in time; determining from the expiratory $CO_2$ measurements a change in alveolar $CO_2$ of the subject between the first and second points in time; and determining a second and updated value of cardiac output or EPBF of the subject based on the first value and the change in alveolar $CO_2$.

11 Claims, 1 Drawing Sheet

(51) Int. Cl.
  *G16H 40/63* (2018.01)
  *A61B 5/087* (2006.01)
  *A61B 5/08* (2006.01)
  *A61B 5/083* (2006.01)
  *A61B 5/00* (2006.01)
  *G16H 20/40* (2018.01)

(52) U.S. Cl.
  CPC .......... *A61B 5/0813* (2013.01); *A61B 5/0836* (2013.01); *A61B 5/7275* (2013.01); *G16H 20/40* (2018.01); *G16H 40/63* (2018.01); *A61B 5/0833* (2013.01); *A61M 2230/04* (2013.01); *A61M 2230/43* (2013.01); *A61M 2230/432* (2013.01)

(58) Field of Classification Search
  CPC .............. A61M 16/00; A61M 16/0057; A61M 16/022; A61M 16/024; A61M 2230/04; A61M 2230/43; A61M 2230/432
  See application file for complete search history.

(56) References Cited

U.S. PATENT DOCUMENTS

| | | | | |
|---|---|---|---|---|
| 6,102,868 A | * | 8/2000 | Banner | A61B 5/0836 600/481 |
| 6,210,342 B1 | * | 4/2001 | Kuck | A61B 5/0836 128/204.23 |
| 6,217,524 B1 | * | 4/2001 | Orr | A61B 5/0836 128/204.12 |
| 2002/0174866 A1 | * | 11/2002 | Orr | A61B 5/029 128/200.24 |
| 2011/0004108 A1 | * | 1/2011 | Peyton | A61M 16/107 600/484 |
| 2013/0109978 A1 | * | 5/2013 | Fisher | A61B 5/7278 600/484 |
| 2013/0253359 A1 | * | 9/2013 | Emtell | A61M 16/0051 600/532 |

* cited by examiner

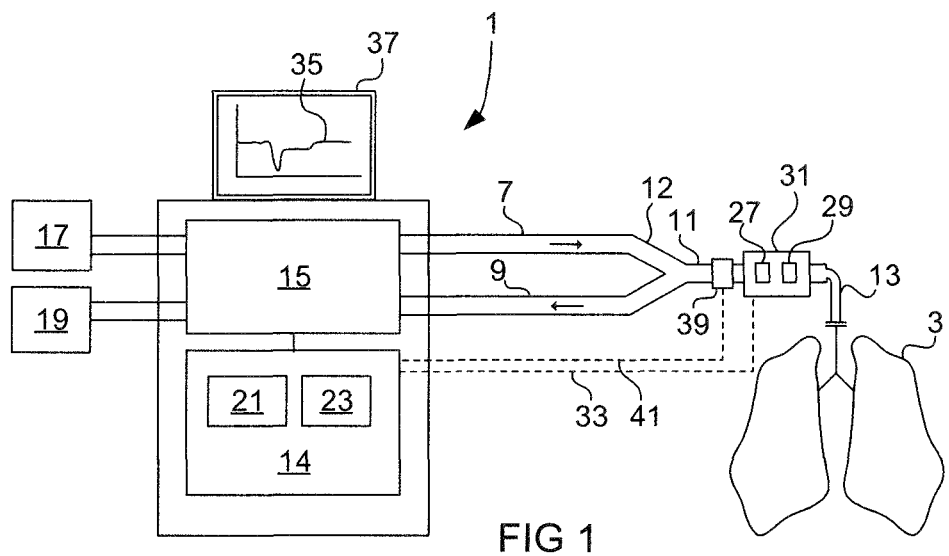
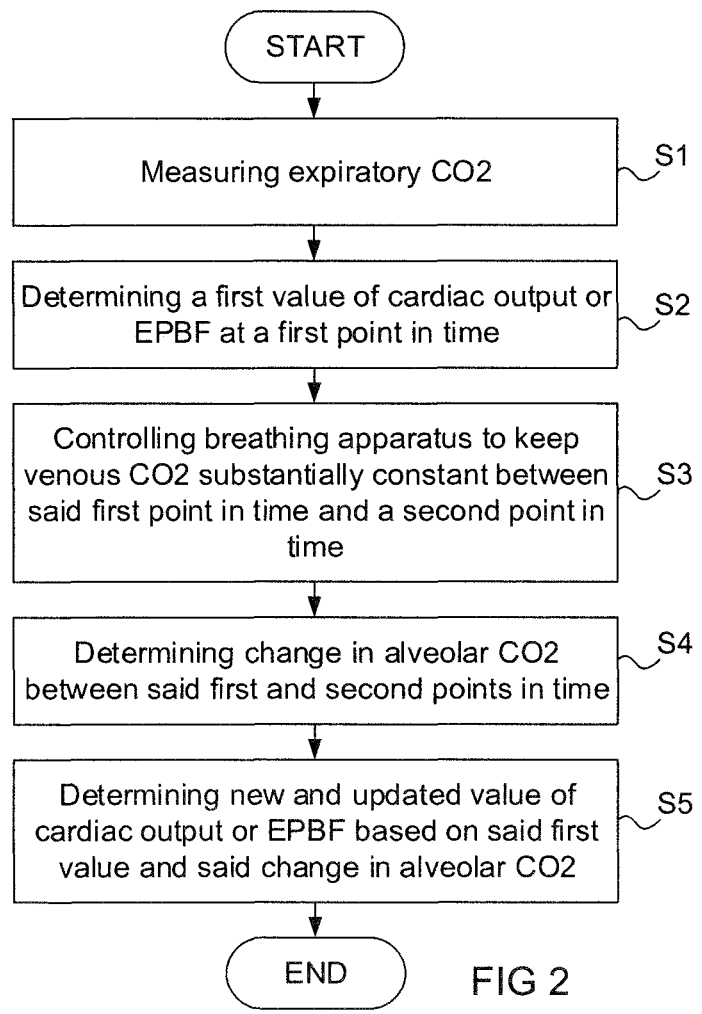

CAPNOTRACKING OF CARDIAC OUTPUT OR EFFECTIVE PULMONARY BLOOD FLOW DURING MECHANICAL VENTILATION

TECHNICAL FIELD

The present disclosure relates to a method, a computer program and a breathing apparatus for determination of cardiac output or effective pulmonary blood flow of a mechanically ventilated subject.

BACKGROUND

Monitoring of cardiac output and EPBF (effective pulmonary blood flow) is important when the cardiovascular stability of a subject is potentially threatened, e.g., during surgery or in critically ill patients. Therefore, it is often desired to monitor the cardiac output and/or the EPBF of mechanically ventilated patients.

Most non-invasive respiratory based methods for determination of cardiac output or EPBF are based on some form of the basic physiological principle known as the Fick principle. According to the Fick equation, the cardiac output of a patient may be determined using the following basic relationship:

$$Q = \frac{VCO2}{(CvCO2 - CaCO2)} \quad \text{Eq. 1}$$

where Q is cardiac output, VCO2 is the volume of carbon dioxide excreted from the body of a patient during respiration (carbon dioxide elimination), CvCO2 is the carbon dioxide concentration in venous blood of the patient, and CaCO2 is the carbon dioxide concentration in arterial blood of the patient.

As well known in the art, EPBF is directly derivable from the cardiac output as:

$$Q \cdot (1-fs) = EPBF \quad \text{Eq. 2}$$

where fs is the pulmonary shunt fraction.

Most methods for cardiac output or EPBF determination employ differential Fick techniques based on the premise that cardiac output and EPBF can be estimated from measurable changes in CO2 elimination (VCO2) and partial pressure of CO2 of expired alveolar gas (PACO2). The measurable changes in VCO2 are normally introduced by changing the effective ventilation of the patient, meaning that the cardiac output or the EPBF of the mechanically ventilated subject is determined from an analysed sequence of breaths during which the effective ventilation of the patient is changed to cause a change in VCO2. The calculations for determination of cardiac output or EPBF and the ventilation pattern employed to cause the change in VCO2 may vary. Examples of calculations and ventilation patterns employed in prior art are described in e.g., WO 2006/119546, U.S. Pat. No. 7,135,001, WO2013/141766, EP2799008 and PCT/SE2015/051357.

Most of the above-identified Fick based methods allow for cardiac output or EPBF to be determined continuously, i.e., on a breath by breath basis, as long as the patient is ventilated using a cyclic ventilation pattern that is adapted to cause sufficient changes in VCO2.

However, during mechanical ventilation, there is sometimes a need for changing the effective ventilation of the patient in a manner that is not commensurate with the ventilation pattern required for continuous Fick based determination of cardiac output or EPBF, i.e., in a way that does not allow cardiac output or EPBF to be determined from measured changes in VCO2. For example, interruption of the cyclic ventilation pattern required for Fick based cardiac output or EPBF determination may be required for the carrying out of blood gas withdrawal or other diagnostic or therapeutic interventions on the ventilated patient. Alternatively, the measurement signals used for the Fick based determination may, during certain circumstances, be lost or deteriorated to an extent rendering cardiac output or EPBF determination impossible. This may be the case, e.g., in a situation in which a surgeon affects the breath-by-breath cardiac output of the ventilated patient in a manner making the level of expired CO2 fall outside the operating range of the Fick method.

To be able to estimate the cardiac output or EPBF of the patient also in situations where Fick based techniques cannot be used, various tracking techniques for tracking breath-to-breath changes in cardiac output or EPBF have been proposed. Once a first (baseline) value of cardiac output or EPBF has been determined using, e.g., a Fick based method, the tracking techniques can be used to provide breath-by-breath estimates of cardiac output or EPBF even if the cyclic ventilation pattern is interrupted.

An example of such a tracking technique is disclosed in WO 2006/119546, wherein a baseline measure of cardiac output and a "continuity equation" for determining breath-by-breath changes in EPBF is used for continuous, non-invasive monitoring of cardiac output. This method is referred to as the "capnotracking method" as it uses CO2 measurements in the cardiac output determination. A similar tracking technique is disclosed in WO2009/062255. Yet other examples of tracking techniques for continuous determination of cardiac output or EPBF are discussed in U.S. Pat. No. 6,217,524 and EP1238631. In all of these tracking techniques, breath-by-breath changes in cardiac output or EPBF are calculated from measured changes in VCO2.

SUMMARY OF THE DISCLOSURE

The present disclosure relates to at least alternative technique for continuous (breath-by-breath) determination of the cardiac output or EPBF of a mechanically ventilated subject.

In particular, the present disclosure relates to a technique for continuous determination of cardiac output or EPBF which can be used in situations where the ventilation pattern currently applied to the ventilated patient does not allow conventional Fick based techniques to be used for cardiac output or EPBF determination.

According to one aspect of the present disclosure, a method for determination of cardiac output or EPBF during mechanical ventilation of a subject, includes the steps of:

measuring expiratory CO2 of the subject, i.e., the CO2 content of expiration gas expired by the subject;

determining, at a first point in time, a first value of cardiac output or EPBF of the subject;

controlling the mechanical ventilation of the subject to keep a level of venous CO2 of the subject substantially constant between the first point in time and a second point in time;

determining, from the expiratory CO2 measurements, a change in alveolar CO2 of the subject between the first and second points in time, and determining a second and updated value of cardiac output or EPBF of the subject based on the first value of cardiac output or EPBF and the change in alveolar CO2.

In accordance with certain embodiments of this disclosure, the level of venous CO2 of the subject is kept substantially constant by determining the CO2 elimination (VCO2) of the subject and using VCO2 as control parameter when controlling the mechanical ventilation of the subject. The VCO2 of the subject may be determined from the expiratory CO2 measurements together with expiratory flow measurements. In some embodiments, expiratory flow measurements may also be used together with the expiratory CO2 measurements in the determination of the change in alveolar CO2.

If the metabolic production of CO2 of the ventilated subject is constant during the relevant time period, the level of venous CO2 will remain constant as long as the CO2 elimination of the subject remains constant. Therefore, in embodiments in which the metabolic production of CO2 is or is assumed to be constant, the level of venous CO2 may be kept substantially constant by controlling the mechanical ventilation of the subject to keep VCO2 substantially constant between the first and second points in time.

In other embodiments of this disclosure, the method may be adapted to take variations in metabolic production of CO2 of the ventilated subject into account. In this scenario, the method may comprise the additional steps of measuring flow and oxygen content of respiration gases, and determining the O2 consumption (VO2) of the subject based on the measured flow and O2 content. Preferably, but not necessarily, the O2 consumption of the subject is determined from measurements of both inspiratory and expiratory flow and O2 content. The level of venous CO2 may then be kept substantially constant by controlling the mechanical ventilation of the subject in a manner causing VCO2 to vary in proportion to VO2 between the first and second points in time.

When changes in cardiac output or EPBF of the ventilated subject occur, e.g., due to changes in fluid status, ventilator settings, intrapulmonary shunt or due to surgical interventions in the subject, the transport of CO2 from the blood to the lung of the subject becomes affected. This change in CO2 transport in turn changes the level of alveolar CO2 and the VCO2 of the subject. While known techniques for capnotracking of cardiac output or EPBF use this change in VCO2 to calculate changes in cardiac output or EPBF, the proposed technique uses a fundamentally different approach by keeping VCO2 constant (or constant in relation to the oxygen consumption of the ventilated subject) through active control of the breathing apparatus mechanically ventilating the subject. This is advantageous in that changes in cardiac output or EPBF can be determined from changes in alveolar CO2 alone. Another advantage of the proposed capnotracking technique is that that venous CO2 content does not have to be determined on a breath-by-breath basis since the mechanical ventilation of the subject is controlled to prevent any changes therein.

Thus, according to the present disclosure, when changes in cardiac output or EPBF occur, the mechanical ventilation of the subject is changed to prevent changes in venous CO2, thereby allowing the changes in cardiac output or EPBF to be quantified from changes in alveolar CO2 alone.

The change in mechanical ventilation typically involves a change in the duration and/or volume of breaths delivered by the breathing apparatus to the subject, e.g., a change in respiratory rate (RR) or tidal volume (VTi). Consequently, in some embodiments, the method comprises the steps of measuring VCO2 of the ventilated subject and controlling the breathing apparatus to keep VCO2 substantially constant, or constant in relation to a measured oxygen consumption of the subject, by adjusting any or both of the duration and volume of breaths delivered by the breathing apparatus.

The first value of cardiac output or EPBF determined at the first point in time can be said to represent a baseline level of cardiac output or EPBF, serving as a starting point for determination of the new and updated value of cardiac output or EPBF. The proposed method thus presents a type of capnotracking technique for continuous cardiac output or EPBF determination, which may be employed once a first "baseline value" of cardiac output or EPBF has been established.

The first value of cardiac output or EPBF may be determined using any known technique for cardiac output or EPBF determination. In accordance with certain embodiments of this disclosure, the first value is determined using a non-invasive technique for cardiac output or EPBF since this makes the method completely non-invasive. In accordance with a particular embodiment, the first value of cardiac output or EPBF of the ventilated subject is determined from the expiratory flow and CO2 measurements using a Fick based technique, such as a differential Fick technique. For example, the first value of cardiac output or EPBF may be determined using the Fick based techniques disclosed in any of the above mentioned WO 2006/119546, U.S. Pat. No. 7,135,001, WO2013/141766, EP2799008 and PCT/SE2015/051357. For even more accurate cardiac output or EPBF determination taking relative variations in cardiac output or EPBF during the sequence of analysed breaths into account, the first value may be determined using the Fick based technique disclosed in the unpublished, co-pending patent application PCT/SE2016/050402.

It is contemplated by the present disclosure that any of the above mentioned Fick based techniques may be used for continuous (breath-by-breath) determination of the cardiac output or EPBF of a ventilated subject during periods of ventilation (hereinafter referred to as Fick phases) in which the subject can be ventilated using a ventilation pattern allowing cardiac output or EPBF to be determined using the Fick based technique, whereas the proposed capnotracking technique may be used for determination of the cardiac output or EPBF of the ventilated subject in a capnotracking phase following one of the Fick phases using a value of cardiac output or EPBF determined during the Fick phase as a starting point or baseline value for capnotracking.

The above described method is typically a computer-implemented method that is carried out through execution of a computer program. Thus, according to another aspect of the present disclosure there is provided a computer program for determination of cardiac output or EPBF of a mechanically ventilated subject. The computer program comprises computer program code segments which, when executed by a processing unit, i.e., a processor, of the above mentioned breathing apparatus, cause the breathing apparatus to:

measure expiratory CO2 of the subject;
determine, at a first point in time, a first value of cardiac output or EPBF of the subject;
control the mechanical ventilation of the subject to keep a level of venous CO2 substantially constant between the first point in time and a second point in time;
determine, from the expiratory CO2 measurements, a change in alveolar CO2 of the subject between the first and second points in time, and determine a second and updated value of cardiac output or EPBF of the ventilated subject based on the first value and the change in alveolar CO2.

The computer program may further comprise program code segments for determining the cardiac output or EPBF of the ventilated subject in accordance with any of the above described principles.

According to yet another aspect of the present disclosure there is provided a non-volatile memory storing the computer program.

According to yet another aspect of the present disclosure there is provided a breathing apparatus, such as a ventilator or an anaesthesia machine, configured to carry out the above described method for determination of cardiac output or EPBF of a mechanically ventilated subject.

To this end, the breathing apparatus comprises a CO2 sensor for measuring expiratory CO2 of the subject, and a control unit configured to determine, at a first point in time, a first value of cardiac output or EPBF of the subject, the control unit being configured to:
- control the mechanical ventilation of the subject to keep a level of venous CO2 of the subject substantially constant between the first point in time and a second point in time;
- determine, from the expiratory CO2 measurements, a change in alveolar CO2 of the subject between the first and second points in time, and
- determine a second and updated value of cardiac output or EPBF of the subject based on the first value and the change in alveolar CO2.

In accordance with certain embodiments of this disclosure, the control unit is configured to use a measure of CO2 elimination (VCO2) of the subject as control parameter to keep the level of venous CO2 substantially constant. To this end, the control unit may be configured to determine the VCO2 of the subject from the expiratory CO2 measurements together with expiratory flow measurements, which expiratory flow measurements, in some embodiments, are obtained by a flow sensor of the breathing apparatus. The expiratory flow measurements may also be used by the control unit, together with the expiratory CO2 measurements, in the determination of the change in alveolar CO2.

In accordance with an embodiment of this disclosure, the control unit is configured to keep the level of venous CO2 substantially constant by controlling the mechanical ventilation to keep the VCO2 of the subject substantially constant between the first and second points in time, or to keep the VCO2 of the subject substantially constant in relation to a measured oxygen consumption of the subject.

More advantageous aspects of the proposed method, computer program and breathing apparatus will be described in the detailed description of embodiments following hereinafter.

BRIEF DESCRIPTION OF THE DRAWINGS

Embodiments of this disclosure will become more fully understood from the detailed description provided hereinafter and the accompanying drawings which are given by way of illustration only. In the different drawings, same reference numerals correspond to the same element.

FIG. 1 illustrates a breathing apparatus according to an exemplary embodiment of the present disclosure, and FIG. 2 is a flow chart illustrating a method for determination of cardiac output or EPBF of a mechanically ventilated subject, according to an exemplary embodiment of the present disclosure.

DETAILED DESCRIPTION

FIG. 1 illustrates a breathing apparatus 1 configured for determination of cardiac output or EPBF of a mechanically ventilated subject 3, hereinafter sometimes referred to as the patient, in accordance with a non-limiting, illustrating embodiment of the present disclosure. The breathing apparatus 1 may be a ventilator, an anaesthesia machine or any other breathing apparatus adapted for mechanical ventilation of a subject in need of respiratory support.

The breathing apparatus 1 is connected to the patient 3 via an inspiratory line 7 for supplying breathing gas to the patient 3, and an expiratory line 9 for conveying expiration gas away from the patient 3. The inspiratory line 7 and the expiratory line 9 are connected to a common line 11, via a so called Y-piece 12, which common line is connected to the patient 3 via a patient connector 13, such as a facemask or an endotracheal tube.

The breathing apparatus 1 further comprises a control unit 14, such as a control computer, for controlling the ventilation of the patient 3 based on preset parameters and/or measurements obtained by various sensors of the breathing apparatus. The control unit 14 controls the ventilation of the patient 3 by controlling a pneumatic unit (i.e. a gas regulator) 15 of the breathing apparatus 1, which pneumatic unit 15 is connected, on one hand, to one or more gas sources 17, 19 and, on the other hand, to the inspiratory line 7 for regulating a flow and/or pressure of breathing gas delivered to the patient 3. To this end, the pneumatic unit 15 may comprise various gas mixing and regulating means well known in the art of ventilation, such as gas mixing chambers, controllable gas mixing valves and one or more controllable inspiration valves.

The control unit 14 comprises a processing unit 21 and a non-volatile memory device 23 storing a computer program for determining the cardiac output or EPBF of the patient 3 according to the principles described herein. Unless stated otherwise, actions and method steps described hereinafter are performed by, or caused by, the control unit 14 of the breathing apparatus 1 upon execution by the processing unit 21 of different code segments of the computer program stored in the memory 23.

The breathing apparatus 1 further comprises at least one flow sensor 27 for measuring at least an expiratory flow of expiration gas exhaled by the patient 3, and at least one CO2 sensor 29 for measuring the CO2 content of at least the expiration gas exhaled by the patient. The control unit 14 is configured to determine the cardiac output or EPBF of the patient 3 based on the CO2 measurements obtained by the CO2 sensor, as will be described in more detail below. Also the measurements of expiratory flow obtained by the flow sensor 27 may be used by the control unit 14 in the cardiac output or EPBF determination. Preferably, the flow and CO2 sensors 27, 29 are configured to measure also inspiratory flow and CO2 content.

In the illustrated embodiment, the flow sensor 27 and the CO2 sensor 29 form parts of a capnograph 31 configured for volumetric capnography measurements. The capnograph 31 is arranged in the proximity of the airway opening of the patient 3, namely, in the common line 11 of the breathing circuit in which it is exposed to all gas exhaled and inhaled by the patient 3. The capnograph 31 is connected to the breathing apparatus 1 via a wired or wireless connection 33, and configured to communicate the result of the flow and CO2 measurements to the breathing apparatus for further processing by the processing unit 21. The breathing apparatus 1 may be configured to generate a volumetric capnogram 35 from the flow and CO2 measurements received from the capnograph 31, and, additionally, to display the volumetric capnogram 35 on a display 37 of the breathing apparatus.

Additionally, the breathing apparatus 1 may comprise an oxygen sensor 39 for measuring inspiratory O2, i.e., the O2 content of the breathing gas delivered to the patient 3 during inspiration, as well as expiratory O2, i.e., the O2 content of the expiration gas exhaled by the patient during expiration. The oxygen sensor 39 is connected to the breathing apparatus 1 via a wired or wireless connection 41, and configured to communicate the result of the O2 measurements to the breathing apparatus for further processing by the processing unit 21. In embodiments taking variations in the metabolic production of CO2 into account, the processing unit 21 may be configured to use the O2 measurements obtained by the O2 sensor 39 to determine the O2 consumption of the patient 3, and to use the O2 consumption in the determination of the cardiac output or EPBF of the patient 3, as will be described in more detail below.

In a preferred embodiment, the control unit 14 is configured to determine a first value, or baseline value, of cardiac output or EPBF of the patient 3 from the flow and CO2 measurements obtained by the flow and CO2 sensors 27, 29 using a non-invasive respiratory based method, preferably a Fick method.

Fick based determination of cardiac output or EPBF typically requires the level of expired CO2 to change with at least 0,2% and preferably around 0,5% or more during the analysed sequence of breaths. To this end, the control unit 14 is configured to introduce a change in the effective ventilation of the patient 3 by changing one or more breathing apparatus settings controlling the ventilation of the patient 3, and to determine the cardiac output or EPBF of the patient based on the flow and CO2 measurements obtained during an analysed sequence of breaths during which the change in effective ventilation occurs.

As in most Fick based methods for cardiac output determination, the analysed sequence of breaths may comprise any number of breaths but typically comprises 4 to 20 breaths, and preferably 4 to 12 breaths. The analysed sequence of breaths comprises at least one phase of increased ventilation and at least one phase of decreased ventilation, wherein each phase of increased and decreased ventilation comprises at least one breath, typically at least two breaths, and preferably two to six breaths. The transition from the phase of increased ventilation to the phase of decreased ventilation, and vice versa, is effectuated by the change in effective ventilation of the patient 3. The change in effective ventilation may be caused by the control unit 14 in any manner known in the art, e.g., by changing the duration and/or the tidal volume of the breaths delivered to the patient by the breathing apparatus.

Preferably, in order to determine cardiac output or EPBF continuously using a Fick based technique, the breathing apparatus 1 is configured to ventilate the patient 3 using a cyclic ventilation pattern comprising alternating phases of decreased and increased ventilation, wherein each phase of decreased ventilation is immediately followed by a phase on increased ventilation, and vice versa. Preferably but not necessarily, the number of breaths in each cycle of the cyclic ventilation pattern corresponds to the number of breaths in the analysed sequence of breaths.

Thus, the breathing apparatus 1 is preferably configured to ventilate the patient 3 using a cyclic ventilation pattern comprising alternating phases of increased and decreased ventilation, and to determine the cardiac output or EPBF of the patient 3 from expiratory flow and CO2 measurements obtained during an analysed sequence of breaths, e.g., a sequence of ten breaths. For example, the control unit 14 may be configured to determine the cardiac output or EPBF of the patient 3 from the analysed sequence of breaths using any of the techniques described in WO 2006/119546, U.S. Pat. No. 7,135,001, WO2013/141766, EP2799008, PCT/SE2015/051357, or the co-pending application PCT/SE2016/050402. By replacing the measurements obtained during the oldest breath in the analysed sequence of breaths with measurements obtained during the most recent breath delivered by the breathing apparatus, an updated value of cardiac output or EPBF can be determined continuously, i.e., on a breath-by-breath basis.

If, due to the clinical situation at hand, the cyclic ventilation pattern can no longer be used or in the event the Fick based technique fails to determine or reliably determine the cardiac output or EPBF of the ventilated patient 3, the control unit 14 of the breathing apparatus 1 is configured to switch from the above described Fick based determination of cardiac output or EPBF to a capnotracking technique for determination of cardiac output or EPBF in accordance with the principles of the present disclosure. Hereinafter, the phase during which cardiac output or EPBF is determined using the Fick based technique will be referred to as the Fick phase, whereas the following phase during which cardiac output or EPBF is determined using the proposed capnotracking technique will be referred to as the capnotracking phase.

In the capnotracking phase, the control unit 14 may be configured to use a value of cardiac output or EPBF determined during the preceding Fick phase as a baseline value of cardiac output or EPBF, which value serves as a starting point for the capnotracking. For example, the baseline value may be the most recent value of cardiac output or EPBF determined during the preceding Fick phase. In one embodiment, the Fick based determination of cardiac output or EPBF is made using any of the techniques disclosed in WO2013/141766 and PCT/SE2015/051357, which is advantageous in that these methods allow the effective lung volume (ELV) and the venous CO2 content (CvCO2) of the patient 3 to be determined at the same time as the cardiac output or EPBF. As will become apparent from the description following hereinafter, CvCO2 will remain constant during the entire capnotracking phase and so does not need to be calculated again.

When switching from the Fick phase to the capnotracking phase, the control unit 14 starts to control the breathing apparatus 1 to keep the level of venous CO2 of the patient 3 substantially constant and equal to the level of venous CO2 at the time of determination of the baseline value of cardiac output or EPBF. This is typically achieved by the control unit 14 by controlling the breathing apparatus 1 based on the CO2 elimination (VCO2) of the patient 3, as determined from the flow and CO2 measurements obtained by the flow and CO2 sensors 27 and 29.

If the metabolic production of CO2 of the patient is or can be assumed to be constant, the venous CO2 content of the patient 3 will remain constant as long as VCO2 remains constant, which allows the control unit 14 to keep the venous CO2 content of the patient 3 at a substantially constant level by controlling the breathing apparatus 1 to keep measured VCO2 substantially constant. In this scenario, the breathing apparatus 1 can be controlled based on expiratory flow and CO2 measurements alone.

If, in this scenario, the cardiac output or EPBF of the patient 3 should change during capnotracking, the alveolar CO2 of the patient will also change while VCO2 is kept constant by adjusting the alveolar ventilation of the patient 3 through active control of the breathing apparatus 1, e.g., by adjusting the respiratory rate or the tidal volume of breaths delivered by the breathing apparatus. This allows the control unit 14 to determine a new and updated value of cardiac output or EPBF from the baseline value of cardiac output or EPBF and the change in alveolar CO2 content, as determined from the CO2 measurements obtained by the CO2 sensor 29. The rationale behind this will be better understood in view of the following relationships.

First it should be noted that, given a constant level of CO2 in the lungs of the patient 3, the respiratory based CO2 elimination, VCO2, balancing out the delivery of CO2 from the blood to the lungs, depends on the difference between venous CO2 content, CvCO2, and pulmonary capillary CO2 content, CcCO2, according to:

$$VCO2 = EPBF \cdot (CvCO2 - CcCO2) \qquad \text{Eq. 3}$$

where $CvCO2 - CcCO2$ ($=\Delta CvcCO2$) is the difference between venous and pulmonary capillary CO2 content.

If VCO2 is kept constant while the EPBF and the alveolar CO2 content of the ventilated patient vary, equation 3 can be used to describe a relation between two different states between which the venous CO2 content, CvCO2, is also assumed to be kept constant and equal to a value $CvCO2_0$, according to:

$$VCO2_0 = EPBF(t) \cdot (CvCO2_0 - CcCO2(t)) = EPBF_0 \cdot (CvCO2_0 - CcCO2_0) \qquad \text{Eq. 4}$$

In equation 4, subscript "0" indicates values of the respective quantities at the point in time for determination of baseline value of EPBF, $EPBF_0$, i.e., the point in time for the Fick based determination serving as starting point for capnotracking. $EPBF_0$ is typically the most recent EPBF value determined during the Fick phase, or the most recent sufficiently reliable EPBF value determined during the Fick phase.

The new and updated value of EPBF is the quantity denoted $EPBF(t)$ in equation 4. By rearranging equation 4, $EPBF(t)$ can be expressed in terms of quantities with subscript 0 and the varying pulmonary capillary CO2 content, $CcCO2(t)$, which can be determined breath by breath from the expiratory CO2 measurements, in accordance with:

$$EPBF(t) = EPBF_0 \cdot \frac{CvCO2_0 - CcCO2_0}{CvCO2_0 - CcCO2(t)} \qquad \text{Eq. 5}$$

By introducing $\Delta CvcCO2_0 = CvCO2 - CcCO2_0$, equation 5 can be expressed as:

$$EPBF(t) = EPBF_0 \cdot \frac{\Delta CvcCO2_0}{\Delta CvcCO2_0 + CcCO2_0 - CcCO2(t)} \qquad \text{Eq. 6}$$

An advantage of this expression is that the pulmonary capillary CO2 difference, $CcCO2_0 - CcCO2(t)$, can be expressed in terms of partial pressure of pulmonary capillary CO2 (PcCO2) and a coefficient of CO2 solubility in blood ($S_{CO2}$):

$$EPBF(t) = EPBF_0 \cdot \frac{\Delta CvcCO2_0}{\Delta CvcCO2_0 + S_{CO2} \cdot (PcCO2_0 - PcCO2(t))} \qquad \text{Eq. 7}$$

If it is assumed that alveolar CO2 is in equilibrium with pulmonary capillary CO2, a new and updated value of EPBF for breath n, $EPBF_n$, can be determined on a breath-by-breath basis from measured variations in alveolar CO2 (PACO2) together with quantities that are obtainable at the point in time for determination of $EPBF_0$:

$$EPBF_n = EPBF_0 \cdot \frac{\Delta CvcCO2_0}{\Delta CvcCO2_0 + S_{CO2} \cdot (PACO2_0 - PACO2_n)} \qquad \text{Eq. 8}$$

where $PACO2_0$ is the partial pressure of alveolar CO2 at the time for determination of $EPBF_0$ and $PACO2_n$ is the partial pressure of alveolar CO2 at breath n, directly derivable from the measurements of expiratory CO2 obtained by the CO2 sensor 29.

If the CO2 level in the lungs of the patient 3 is in equilibrium at the time for determination of $EPBF_0$, and if a baseline level of CO2 elimination ($VCO2_0$) is determined at the same time from the expiratory flow and CO2 measurements, equation 1 can be used to calculate $dCvcCO2_0$ as:

$$\Delta CvcCO2_0 = \frac{VCO2_0}{EPBF_0} \qquad \text{Eq. 9}$$

Combining equations 8 and 9 yields the following relation which may be advantageously used by the control unit 14 of the breathing apparatus 1 to calculate a new and updated value of EPBF for any given breath n within the capnotracking phase following determination of a baseline value for EPBF, $EPBF_0$:

$$EPBF_n = EPBF_0 \cdot \frac{VCO2_0}{VCO2_0 + EPBF_0 \cdot S_{CO2} \cdot (PACO2_0 - PACO2_n)} \qquad \text{Eq. 10}$$

Thus, according to one embodiment of the present disclosure, the control unit 14 may be configured to determine a first baseline value of EPBF, $EPBF_0$, at a first point in time using any known technique for EPBF determination, such as any of the above discussed Fick based techniques; control the mechanical ventilation of the patient 3 to keep the level of venous CO2 in the patient substantially constant between the first and a second point time, e.g., by adjusting the alveolar ventilation of the patient to keep VCO2 substantially constant; determining a change in alveolar CO2 ($PACO2_0 - PACO2_n$) of the patient between the first and second points in time from the expiratory CO2 measurements, and determining a new and updated value of EPBF, $EPBF_n$, based on the baseline value of EPBF, $EPBF_0$, and the change in alveolar CO2, e.g., by using equation 10.

If using equation 10, the control unit 14 would also need to use an estimate of the CO2 solubility in blood in the determination of the new and updated EPBF value, $EPBF_n$. How to estimate $S_{CO2}$ is well-known in the art, and the control unit 14 may be configured to use any known constant estimate of $S_{CO2}$, or to estimate $S_{CO2}$ from available data using any known technique for $S_{CO2}$ estimation. Constant $S_{CO2}$ estimates and techniques for estimating $S_{CO2}$ have been discussed, e.g., in Gedeon et al., A new method for noninvasive bedside determination of pulmonary blood flow, Med Biol Eng Comput 1980; 18:411-418, Capek et al., Noninvasive Measurement of Cardiac Output Using Partial CO2 Rebreathing, IEEE Transactions on Biomedical Engineering, Vol. 35, No. 9, September 1988, and Cecchini et al., Non-invasive Estimation of Cardiac Output in Mechanically Ventilated Patients: A prolonged Expiration Method, Annals of Biomedical Engineering, August 2012, Volume 40, Issue 8, pp 1777-1789. Thus, it should be appreciated that the control unit 14 may be configured to estimate $S_{CO2}$ from available data, e.g., using any of the techniques discussed in the above mentioned publications, or to use a constant estimate of $S_{CO2}$, e.g., an estimate that is manually input to the control unit 14 via a user interface of the breathing apparatus.

The control unit 14 may be configured to use any suitable control algorithm for keeping VCO2 of the patient 3 substantially constant (in case of constant metabolic production of CO2) during the capnotracking phase. In a basic implementation, the control unit 14 may be configured to control the mechanical ventilation of the patient 3 in proportion to VCO2, according to:

$$VA_{n+1} = VA_n \cdot \frac{VCO2_0}{VCO2_n} \qquad \text{Eq. 11}$$

where VCO2 is the CO2 elimination of the patient 3 at the point in time for determination of $EPBF_0$, $VA_n$ and VCO2 is the alveolar ventilation and the CO2 elimination, respectively, of the patient 3 for a subsequent breath n, and $VA_{n+1}$ is the alveolar ventilation to be provided to the patient by the breathing apparatus 1 in a breath n+1 following the subsequent breath n. This means that the mechanical ventilation may be controlled on a breath-by-breath basis during the capnotracking phase such that the alveolar ventilation of the patient 3 for any breath n+1 is based on, and proportional to, the relationship between the baseline VCO2 value, $VCO2_0$, and the VCO2 value, $VCO2_n$, determined for the preceding breath n. As mentioned above, the alveolar ventilation of the patient 3 is preferably adjusted by the control unit 14 by adjusting the respiratory rate (RR) or the tidal volume (VTi) of breaths delivered by the breathing apparatus 1. Most preferably, the respiratory rate is adjusted to achieve the desired alveolar ventilation.

The alveolar ventilation may, as well known in the art, be determined from the tidal volume and the airway deadspace of the patient 3. As also well known in the art, the airway deadspace can be derived using volumetric capnography, and may thus be determined using the capnograph 31 of the breathing apparatus 1.

The above calculations are based on the assumption that the metabolic production of CO2 of the ventilated patient 3 remains substantially constant during the capnotracking phase. If, however, the metabolic CO2 production varies, the venous CO2 content of the patient 3 may vary in an unknown manner even if controlling the breathing apparatus 1 to keep VCO2 substantially constant and equal to $VCO_0$.

Therefore, the proposed capnotracking technique may involve the steps of measuring also the O2 content of respiration gases, and taking the O2 content into account to keep venous CO2 substantially constant during the capnotracking phase.

To this end, the control unit 14 may be configured to determine the metabolic consumption of O2 of the ventilated patient 3 from measured flow and O2 content, and to keep the venous CO2 content of the patient 3 substantially constant during the capnotracking phase by controlling the mechanical ventilation of the patient 3 in a manner causing VCO2 to vary in proportion to the metabolic O2 consumption.

The metabolic production of CO2 is proportional to the metabolic consumption of O2 according to:

$$VCO2_{met} = RQ \cdot VO2_{met} \qquad \text{Eq. 12}$$

where $VCO2_{met}$ is the metabolic production of CO2 of the ventilated subject, VO2 met is the oxygen consumption of the ventilated subject, and RQ is the so called respiratory quotient having a typical value in the range of 0.7-1.0, depending on the composition of the nutrition.

In order to keep the venous CO2 content of the ventilated patient 3 substantially constant during the capnotracking phase, taking variations in the metabolic production of CO2 into account, the control unit 14 may be configured to control the mechanical ventilation of the patient 3 to keep measured VCO2 substantially equal to a variable target value that is calculated based on measured variations in O2 consumption during the capnotracking phase, e.g., according to:

$$VCO2^{target}(t) = VCO2_0 \cdot \frac{VO2(t)}{VO2_0} \qquad \text{Eq. 13}$$

where $VCO2^{target}(t)$ is the target value for CO2 elimination at time t, VO2(t) is the measured O2 consumption at time t, and $VCO2_0$ and $VO2_0$ are the baseline values of VCO2 and VO2 at the time for determination of $EPBF_0$.

The new and updated value of EPBF may then be determined for any given breath n during the capnotracking phase by using the following relation, which corresponds to equation 10 with the exception that the term $VCO2_0$ in the numerator has been replaced with the VO2 dependent target value of CO2 elimination for breath n, $VCO2_n^{target}$:

$$EPBF_n = EPBF_0 \cdot \frac{VCO2_n^{target}}{VCO2_0 + EPBF_0 \cdot S_{CO2} \cdot (PACO2_0 - PACO2_n)} \qquad \text{Eq. 14}$$

In other words, a new and updated value of EPBF, $EPBF_n$, may be derived from a baseline value of EPBF, $EPBF_0$, and a measured change in alveolar CO2 ($PACO2_0 - PACO2_n$) using equation 14 which, assuming constant metabolic CO2 production, may be simplified in accordance with equation 10.

FIG. 3 is a flow chart illustrating a method for determination of cardiac output or EPBF of a subject being mechanically ventilated by means of a breathing apparatus, according to an embodiment of the present disclosure.

In a first step, S1, expiratory CO2 of the ventilated subject is measured. In the event VCO2 is used as control parameter for controlling the mechanical ventilation of the subject (see step S3), or in the event expiratory flow is used together with expiratory CO2 in determination of a change in alveolar CO2 (see step S4), also expiratory flow may be measured. As mentioned above, expiratory flow and CO2 may be measured using a capnograph, or the like, such as the capnograph 31 schematically illustrated in FIG. 1, devised to measure flow and CO2 content of expiration gases exhaled by the subject.

In a second step, S2, a first value or baseline value of cardiac output or EPBF of the subject is determined at a first point in time. As mentioned above, this baseline value may be determined using any known technique for cardiac output or EPBF determination, but is preferably determined at least partly from the expiratory flow and CO2 measurements using a non-invasive Fick technique.

In a third step, S3, a capnotracking phase is initiated by starting to control the breathing apparatus to keep the venous CO2 content of the subject at a substantially constant level. As discussed above, this is typically achieved by controlling the breathing apparatus based on measured VCO2 by adjusting the respiratory rate and/or the tidal volume of breaths delivered by the breathing apparatus to keep the measured VCO2 constant, or proportional to measured oxygen consumption by the subject.

In a fourth step, S4, a change in alveolar CO2 content of the subject between the first and second points in time is determined from the expiratory CO2 measurements obtained in step S1. The change may, for example, be determined as a change in partial pressure of CO2 of expired alveolar gas, e.g., measured by the capnograph 31. Expiratory flow measurements may also be used in addition to the expiratory CO2 measurements in the determination of the change in alveolar CO2 content.

In a fifth step, S5, a new and updated value of cardiac output or EPBF is determined based on the first or baseline value of cardiac output or EPBF and the change in alveolar CO2 content. The new and updated value of cardiac output or EPBF may, for example, be calculated based on the relationship expressed by equation 14, possibly simplified in accordance with equation 10.

In a subsequent step (not shown), the new and updated value of cardiac output or EPBF determined in step S5 may be compared with one or more threshold values, defining a recommended and pre-set range for cardiac output or EPBF, whereupon an alarm signal may be generated in response to the comparison should the determined cardiac output or EPBF value fall outside the recommended range.

The method is typically a computer-implemented method, meaning that it is performed through execution of a computer program. As mentioned above, the various method steps are typically performed by, or caused by, the control unit 14 of the breathing apparatus 1 upon execution by the processing unit 21 of different code segments of the computer program, which may be stored in the hardware memory device 23.

Although the proposed capnotracking technique has been described above in conjunction with a Fick based technique for determination of the baseline value of cardiac output or EPBF, it should be emphasized that any known technique for cardiac output or EPBF determination can be used to generate the baseline value. In alternative embodiments, the baseline value may, for example, originate from invasive techniques for cardiac output monitoring, such as invasive pulse contour analysis. Furthermore, the baseline value may be determined automatically by the control unit 14 of the breathing apparatus 1 based on available data, or it may be determined by the control unit 14 based on user input that is input to the control unit 14 by a user or operator via a user interface of the breathing apparatus. Thus, in yet alternative embodiments, the control unit 14 may be configured to receive user input indicating a value of cardiac output or EPBF, and to use this value as a baseline value for cardiac output or EPBF during a subsequent phase of capnotracking of cardiac output or EPBF according to the principles described herein.

Furthermore, although the above calculations have been performed for capnotracking of EPBF, it should be noted that the cardiac output of the ventilated subject can be continuously determined using the same principles. In accordance with equation 2, cardiac output is directly proportional to EPBF in case of constant shunt. The above equations for calculation of EPBF may hence be readily adapted for calculation of cardiac output, taking the pulmonary shunt fraction, fs, into account. The shunt fraction may be estimated by the control unit 14 in any manner known in the art, or an estimate of the shunt fraction may be provided to the control unit 14 by an external device to which the breathing apparatus is connectable, or by a user or operator via a user interface of the breathing apparatus. The shunt fraction may either be assumed to remain constant during the period of capnotracking, or the equations for calculation of a new and updated value of cardiac output may be adapted to take variations in shunt fraction during the capnotracking phase into account in order to further increase the accuracy in cardiac output determination.

The invention claimed is:

1. A method for controlling a breathing apparatus and determining a cardiac output or an Effective Pulmonary Blood Flow ("EPBF") of a mechanically ventilated subject, comprising:

determining, at a first point in time, a first value of cardiac output or EPBF of the subject by a control unit of the breathing apparatus;

measuring, at the first point in time, a first expiratory $CO_2$ content of the subject, wherein the first expiratory $CO_2$ content is measured by at least one $CO_2$ sensor;

controlling a mechanical ventilation of the subject by the control unit adjusting one or more settings of the breathing apparatus so as to keep a level of venous $CO_2$ of the subject substantially constant between the first point in time and a second point in time;

measuring, at the second point in time, a second expiratory $CO_2$ content of the subject, wherein the second expiratory $CO_2$ content is measured by the at least one $CO_2$ sensor;

determining a change in alveolar $CO_2$ content of the subject between the first and second points in time by the control unit based on the first expiratory $CO_2$ content and the second expiratory $CO_2$ content measured by the at least one $CO_2$ sensor, and determining a second value for the cardiac output or the EPBF of the subject by the control unit based on the first value and the change in alveolar $CO_2$ content between the first and second points in time.

2. The method of claim 1, wherein a measure of $CO_2$ elimination of the subject is used by the control unit as control parameter to keep the level of venous $CO_2$ substantially constant between the first and second points in time.

3. The method of claim 2, wherein the level of venous $CO_2$ is kept substantially constant between the first and second points in time by the control unit controlling the mechanical ventilation to keep the $CO_2$ elimination of the subject substantially constant between the first and second points in time, or to keep the $CO_2$ elimination of the subject substantially proportional to a measured oxygen consumption of the subject measured by an oxygen sensor.

4. The method of claim 1, wherein the first value of cardiac output or EPBF is a first value of EPBF and the second value of cardiac output or EPBF is a second value of EPBF, which second value is calculated based on the following relationship:

$$EPBF_n = EPBF_0 \cdot \frac{VCO2_n^{target}}{VCO2_0 + EPBF_0 \cdot S_{CO2} \cdot (PACO2_0 - PACO2_n)}$$

where $EPBF_n$ is the second value of EPBF, $EPBF_0$ is the first value of EPBF, $VCO2_0$ and $PACO2_0$ are the CO2 elimination and partial pressure of alveolar CO2, respectively, of the ventilated subject at the first point in time, $PACO2_n$, is the partial pressure of alveolar CO2 of the ventilated subject at the second point in time, $S_{CO2}$ is the coefficient of CO2 solubility in blood, and $VCO2_n^{target}$ is a target value for the $CO_2$ elimination at the second point in time.

5. The method of claim 4, wherein $VCO2_n^{target}$ is set to $VCO2_0$, assuming constant metabolic production of CO2 of the ventilated subject, or calculated based on a measured change in oxygen consumption of the ventilated subject between the first and second points in time.

6. A non-transitory, computer readable data storage medium with an executable program stored thereon, wherein the program instructs a processing unit of a breathing apparatus to perform operations for controlling the breathing apparatus and determining a cardiac output or an Effective Pulmonary Blood Flow ("EPBF") of a mechanically ventilated subject, when executed by the processing unit, the operations comprising steps to:
  determine, at a first point in time, a first value of cardiac output or EPBF of the subject;
  receive a measure of a first expiratory $CO_2$ content of the subject, measured at the first point in time;
  control a mechanical ventilation of the subject by adjusting one or more settings of the breathing apparatus so as to keep a level of venous $CO_2$ of the subject substantially constant between the first point in time and a second point in time;
  receive a measure of a second expiratory $CO_2$ content of the subject, measured at the second point in time;
  determine a change in alveolar $CO_2$ content of the subject between the first and second points in time based on the first expiratory $CO_2$ content and the second expiratory $CO_2$ content, and
  determine a second value for the cardiac output or the EPBF of the subject based on the first value and the change in alveolar $CO_2$ content between the first and second points in time.

7. A breathing apparatus configured to provide mechanical ventilation to a subject and to determine a cardiac output or an Effective Pulmonary Blood Flow ("EPBF") of the mechanically ventilated subject, comprising a control unit configured to:
  determine, at a first point in time, a first value of cardiac output or EPBF of the subject;
  receive a measure of a first expiratory $CO_2$ content of the subject, measured by at least one $CO_2$ sensor at the first point in time;
  control the mechanical ventilation of the subject to keep a level of venous $CO_2$, of the subject substantially constant between the first point in time and a second point in time;
  receive a measure of a second expiratory $CO_2$ content of the subject, measured by the at least one $CO_2$ sensor at the second point in time;
  determine a change in alveolar $CO_2$ of the subject between the first and second points in time based on the first expiratory $CO_2$ content and the second expiratory $CO_2$ content measured by the at least one $CO_2$ sensor, and
  determine a second value for the cardiac output or the EPBF of the subject based on the first value and the change in alveolar $CO_2$ content between the first and second points in time.

8. The breathing apparatus of claim 7, wherein the control unit is configured to use a measure of $CO_2$ elimination as a control parameter to keep the level of venous $CO_2$ substantially constant between the first and second points in time.

9. The breathing apparatus of claim 8, wherein the control unit is configured to keep the level of venous $CO_2$ substantially constant between the first and second points in time by controlling the mechanical ventilation of the subject to keep the $CO_2$ elimination of the subject substantially constant between the first and second points in time, or to keep the $CO_2$ elimination of the subject substantially proportional to a measured oxygen consumption of the subject, measured by an oxygen sensor of the breathing apparatus.

10. The breathing apparatus of claim 7, wherein the first value of cardiac output or EPBF is a first value of EPBF and the second value of cardiac output or EPBF is a second value of EPBF, the control unit being configured to calculate the second value based on the following relationship:

$$EPBF_n = EPBF_0 \cdot \frac{VCO2_n^{target}}{VCO2_0 + EPBF_0 \cdot S_{CO2} \cdot (PACO2_0 - PACO2_n)}$$

where $EPBF_n$ is the second value of EPBF, $EPBF_0$ is the first value of EPBF, $VCO2_0$ and $PACO2_0$ are the $CO_2$ elimination and partial pressure of alveolar $CO_2$, respectively, of the ventilated subject at the first point in time, $PACO2_n$ is the partial pressure of alveolar $CO_2$ of the ventilated subject at the second point in time, $S_{CO2}$ is the coefficient of $CO_2$ solubility in blood, and $VCO2_n^{target}$ is a target value for the $CO_2$ elimination at the second point in time.

11. The breathing apparatus of claim 10, wherein the control unit is configured to set $VCO2_n^{target}$ to $VCO2_0$, assuming constant metabolic production of $CO_2$ of the ventilated subject, or to calculate $VCO2_n^{target}$ based on a measured change in oxygen consumption of the ventilated subject between the first and second points in time.

* * * * *